(12) United States Patent
Gao (10) Patent No.: US 8,393,254 B2
(45) Date of Patent: Mar. 12, 2013

(54) GRIPPING DEVICE

(75) Inventor: Hua Gao, Fox Point, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 195 days.

(21) Appl. No.: 12/380,823

(22) Filed: Mar. 4, 2009

(65) Prior Publication Data

US 2009/0223332 A1   Sep. 10, 2009

Related U.S. Application Data

(60) Provisional application No. 61/068,032, filed on Mar. 4, 2008.

(51) Int. Cl.
*B25B 7/02* (2006.01)

(52) U.S. Cl. .................. 81/420; 81/64; 81/340; 81/319; 81/323; 294/2

(58) Field of Classification Search ............ 81/314–341, 81/347–351, 362, 386–392, 395, 402; 30/175–176, 30/183–184, 189–193, 197, 226
See application file for complete search history.

(56) References Cited

U.S. PATENT DOCUMENTS

| 475,940 | A | * | 5/1892 | Hamlin | 433/1 |
| 765,328 | A | * | 7/1904 | Stripe | 140/52 |
| 813,598 | A | * | 2/1906 | Sylvester | 30/178 |
| 837,473 | A | * | 12/1906 | Ihrig | 47/1.01 R |
| 914,910 | A | * | 3/1909 | Alley | 30/191 |
| 1,052,982 | A | * | 2/1913 | Sturtevant et al. | 294/2 |
| 1,427,668 | A | * | 8/1922 | Williams | 81/335 |
| 1,610,387 | A | * | 12/1926 | Pennington | 81/64 |
| 1,817,988 | A | * | 8/1931 | Klamt | 81/315 |
| 2,577,638 | A | * | 12/1951 | Tibbetts | 30/193 |
| 5,408,904 | A | * | 4/1995 | Neff | 81/360 |
| 6,212,977 | B1 | * | 4/2001 | Liou | 81/323 |

* cited by examiner

*Primary Examiner* — Monica Carter
*Assistant Examiner* — Melanie Alexander
(74) *Attorney, Agent, or Firm* — Ryan Kromholz & Manion, S.C.

(57) ABSTRACT

A gripping device comprising a first arm pivotally connected to a second arm. The arms form a gripping area. A linkage mechanism is used for adjusting the inwardly and outwardly movement of the gripping area, with the linkage mechanism pivotally connected to the first arm and second arm. The linkage mechanism is formed of a first linkage laterally and pivotally connected to a second linkage.

11 Claims, 7 Drawing Sheets

GRIPPING DEVICE

RELATED APPLICATIONS

This application claims the benefit of U.S. Provisional Patent Application Ser. No. 61/068,032 filed on 4 Mar. 2008 and entitled "Gripping Device."

BACKGROUND OF THE INVENTION

The present invention relates to medical devices and tools and more particularly to medical device and tools that provide a gripping surface such as retractors, clamps, pliers, and other devices.

Precision is a necessity for medical procedures and devices used for those procedures. Because devices are used to grab or grip very sensitive areas of a body, such as when working on veins, arteries, nerves, or other very sensitive areas, devices must be able to be minutely adjustable, while still providing enough gripping strength. Accordingly, it is always desirous to have a gripping device that has improved sensitivity and precision without affecting the gripping strength.

SUMMARY OF THE INVENTION

The present invention is an improved gripping device. The device has a pliers-style shape comprising a gripping area. The device has two arms that are generally connected by a ratcheting device preferably comprising a pawl, that allows the arms to be moved and separated a desired distance. One of the arms is further connected to an adjustment arm that is arranged to be received by a receptacle located on the other arm. The adjustment arm allows for precise adjustment of the gripping area. The ratcheting device and the adjustment device could be combined as a single structure or separate structures.

The two arms are made of separate sections, which are connected to one another by a series of fulcrums. The arrangement of the arms is integrated with a positioning mechanism that provides a multiple scissors effect for movement of the device, which provides improved precision and gripping strength for the device.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

The present invention comprises a gripping device 10, shown and described in FIGS. 1-13. The gripping device 10 generally comprises a gripping area 12 that has a first gripping surface 14 and a second gripping surface 16. The gripping device 10 is arranged and designed so that the gripping area 12 can be adjusted accurately and precisely in a manner that will prevent undesirable movement or inadvertent readjustment of the gripping surfaces 14, 16 when they are spaced apart at a predetermined distance. That is, the device 10 allows for the gripping surfaces 14, 16 to be held in a secure, spaced apart arrangement.

The gripping device further comprises a first arm 18 and a second arm 20 which are principally connected by a fulcrum 22. The fulcrum 22 preferably comprises a screw, bolt, or pin, or another similar device that will allow the arms 18, 20 to pivot with respect to one another. Each of the arms 18, 20 are further connected to a respective secondary pivot 24, 26, which connects the arms 18, 20 to the rear of the gripping surfaces 14, 16 respectively by way of a second fulcrum 27. The arms 18, 20 are further connected to one another by way of a scissors-style positioning member 28, which forms a portion of a linkage mechanism 70 discussed with respect to FIG. 14.

Figures 1, 2:
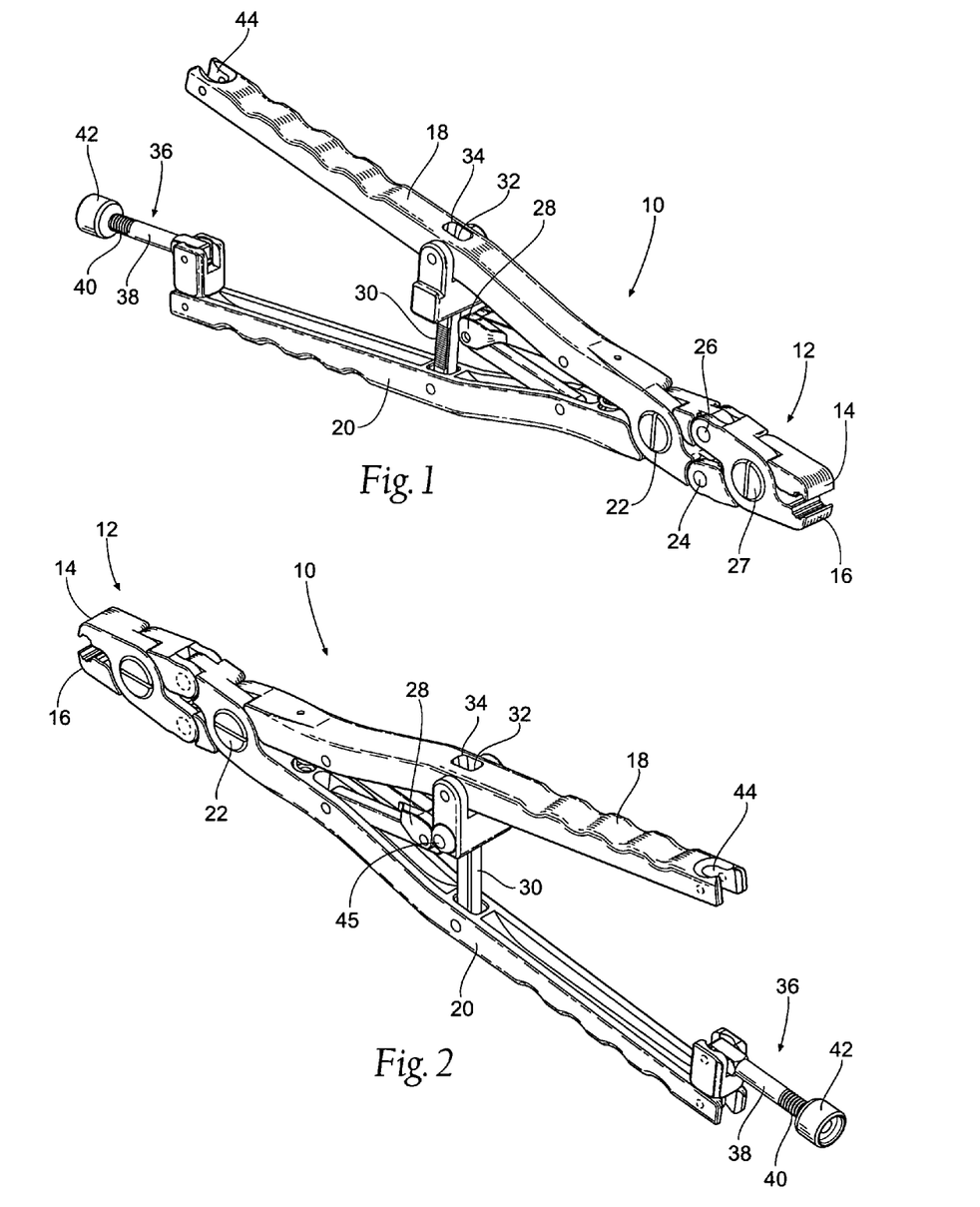
FIG. 1 is a right side perspective-view of a gripping device of the present invention in a first position.
FIG. 2 is a left side perspective view of the gripping device of FIG. 1.
Figure 3:
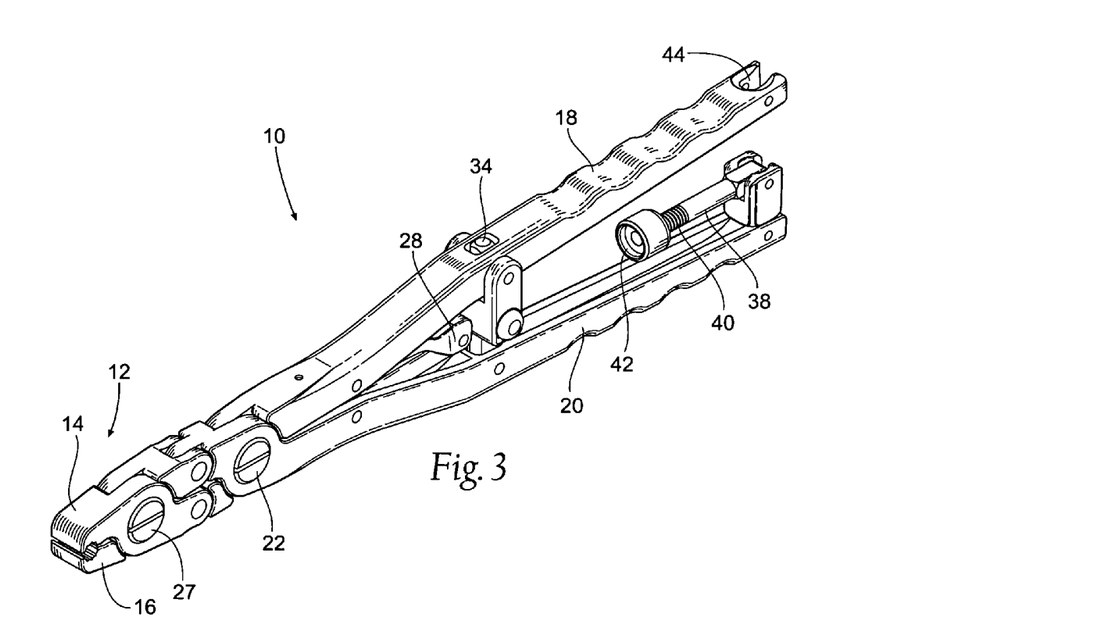
FIG. 3 is a left side perspective view of a gripping device of the present invention in a second position.
Figure 4:
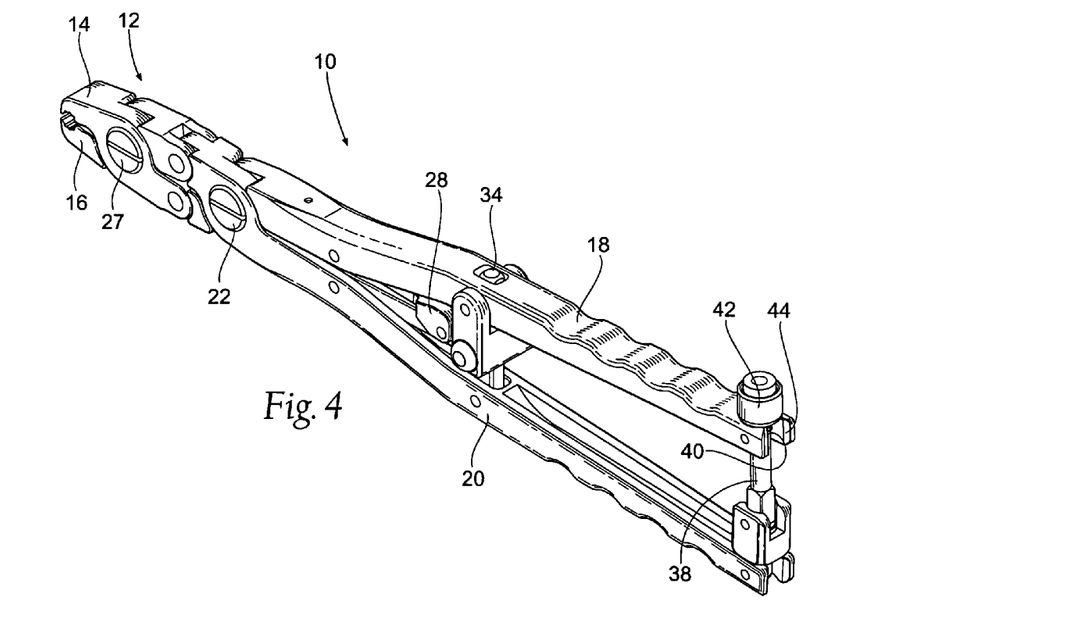
FIG. 4 is a left side perspective view of the gripping device of the present invention in a third position.
Figure 5:
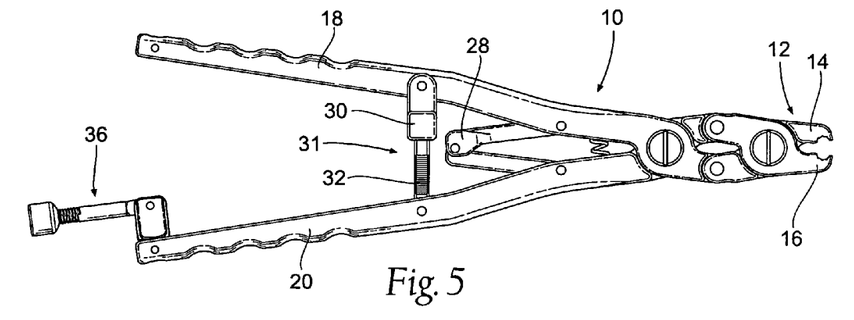
FIG. 5 is a right side view of the gripping device of FIG. 1.
Figure 6:
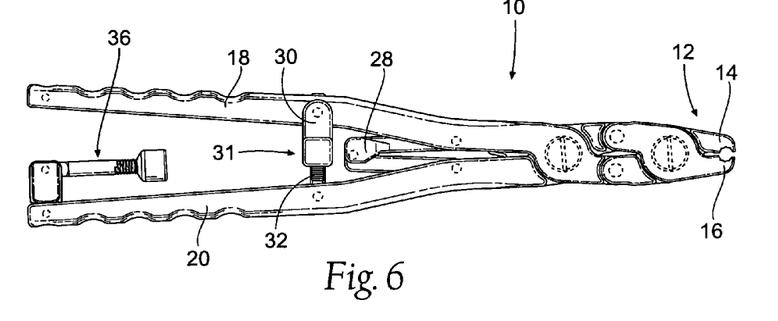
FIG. 6 is a right side view of the gripping device of FIG. 3.
Figure 7:
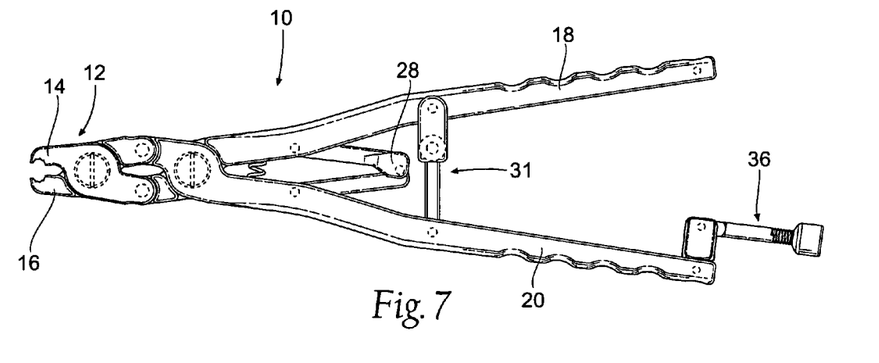
FIG. 7 is a left side view of the gripping device of FIG. 1.
Figure 8:
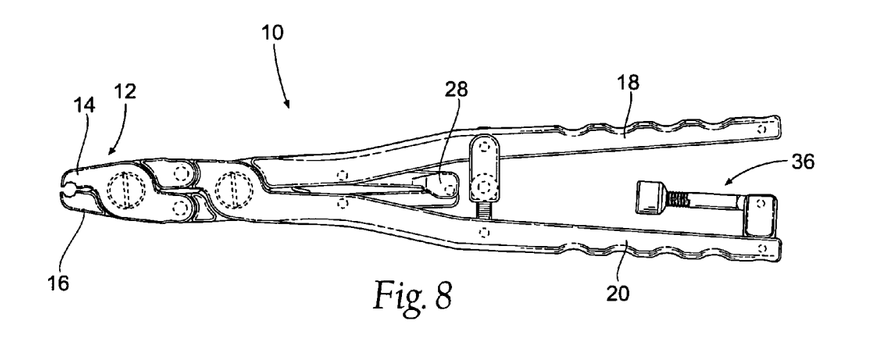
FIG. 8 is a left side view of the gripping device of FIG. 3.
Figure 9:
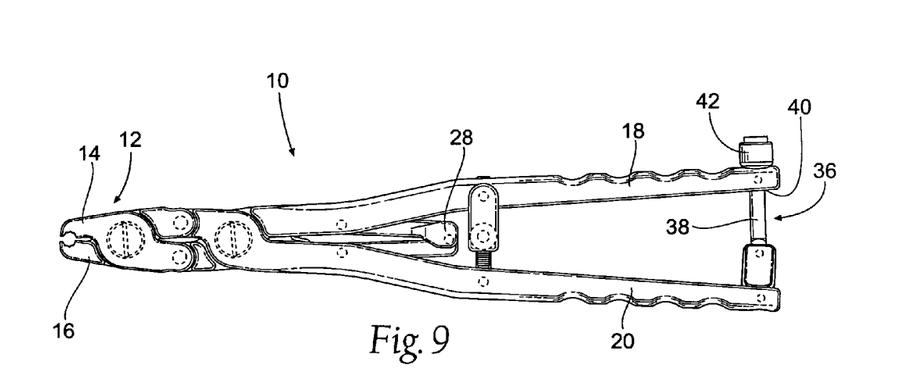
FIG. 9 is a left side view of the gripping device of FIG. 4.
Figure 10:
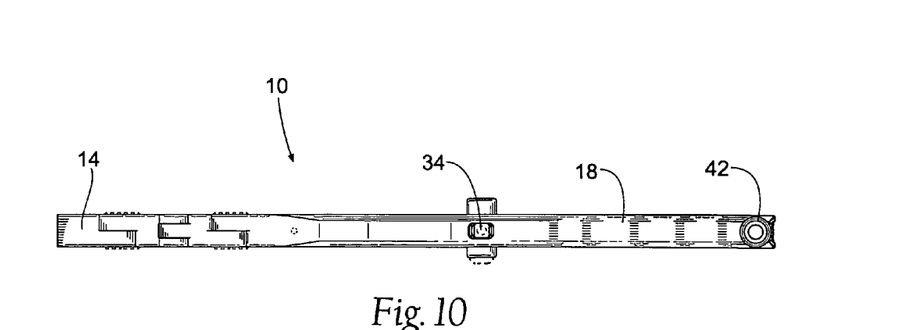
FIG. 10 is a top view of the gripping device of the present invention.
Figure 11:
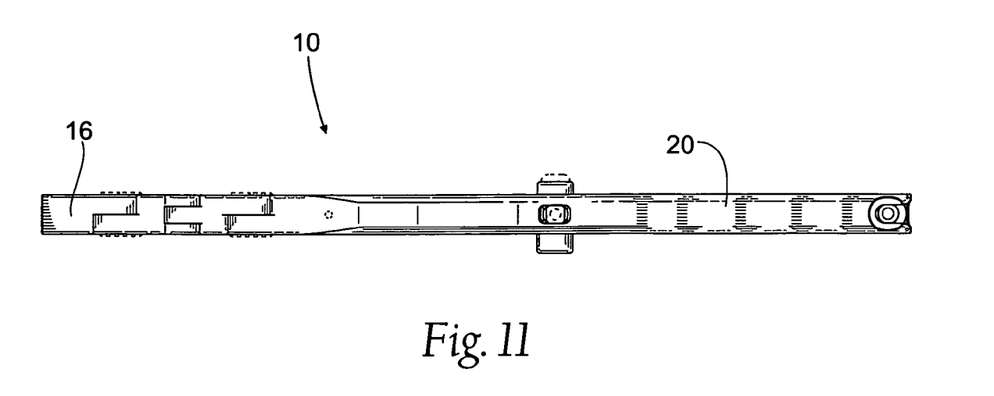
FIG. 11 is a bottom view of the gripping device of the present invention.
Figure 12:
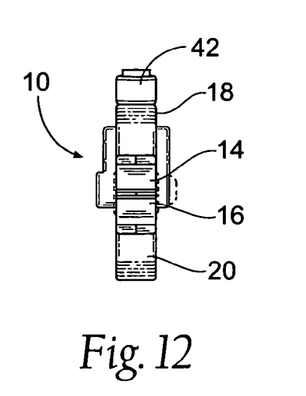
FIG. 12 is a front view of the gripping device of the present invention.
Figure 13:
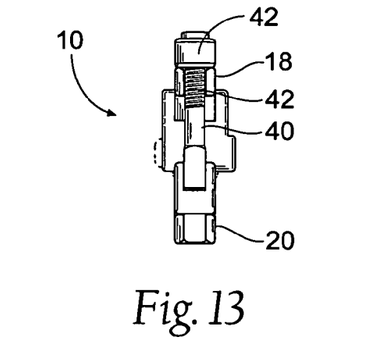
FIG. 13 is a back view of the gripping device of the present invention.

As shown in FIGS. 5, 6 and 7, the device 10 further comprises a ratcheting mechanism 31, which further contributes to the accuracy and precision of the gripping device 10. The ratcheting mechanism 31 generally comprises a pawl 30 attached to the arm 20, which is arranged to interact with notches 32. The arm 18 has an opening 34 (see FIGS. 2 and 3) that will allow the pawl 30 to pass through the arm 18 when the pawl 30 is moved to engage the notches 32. The pawl 30 preferably has a releasable locking arrangement to hold the arms 18 and 20 in a desired spaced apart arrangement. A push button 45 located on the pawl 30 will allow release of the ratcheting mechanism 31 when necessary. It is understood that the pawl 30 and notches 32 could be reversed and that the ratcheting mechanism would fall within the scope of the present invention. Likewise, the ratcheting mechanism 31 (and the push button 45, i.e. release mechanism) could take other forms than the pawl 30 and notches 32 and still fall within the scope of the present invention.

The gripping device 10 further comprises an adjustment arm 36 that is pivotally connected to the arm 20. As demonstrated with respect to FIGS. 7 and 8, the pivotal aspect of the adjustment arm 36 allows the adjustment arm 36 to be folded inwardly or outwardly as desired, which will allow for more efficient storage of the device 10. The adjustment arm 36 generally comprises a shaft 38, a threaded end 40, and an engagement section 42. The engagement section 42 is arranged to removably mate with a receptacle 44 located on the arm 18 (see FIGS. 4 and 9). The adjustment arm 36 could be located on the arm 18 and the receptacle 44 could be located on the arm 20 and the arrangement would still fall within the scope of the present invention. It is also understood that the engagement section 42 and the receptacle 44 could vary in size and shape and still fall within the scope of the present invention.

The gripping device 10 of the present invention provides a solid, sturdy gripping structure, while still being able to be precisely adjusted. The device 10 is capable of being locked securely in a predetermined arrangement, but also can be easily adjusted and readjusted if necessary.

The interaction of the engagement section 42 with the receptacle 44 allows the gripping sections 14, 16 to be precisely moved inwardly and outwardly with respect to one another. The receptacle 44 will securely receive the shaft 38 of the adjustment arm 36, with the engagement section 42 resting upon the arm 18. The user may then rotate the engagement section 42, thereby moving it upwardly or downwardly the threaded section 40, thereby adjusting the distance between the arms 18, 20 and, consequently, adjusting the distance between the gripping sections 14 and 16.

Figure 14:
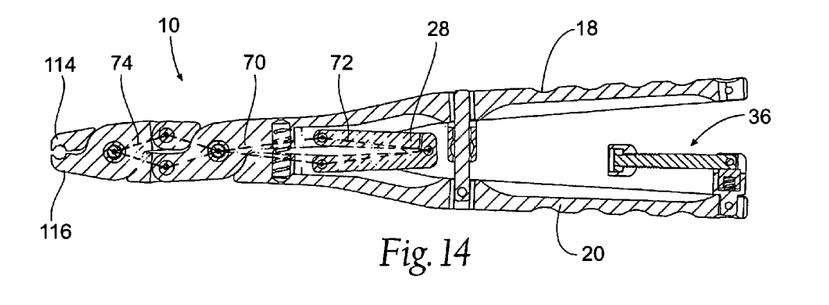
FIG. 14 is a cross-sectional view of the gripping device FIGS. 1-13, demonstrating the linkage mechanism used to control the gripping movement of the device.

A cross-sectional view of the gripping device 10 is shown in FIG. 14. A double linkage positioning mechanism 70 is detailed in the drawing, demonstrated by a dotted line. The linkage mechanism 70 comprises of a first linkage 72 and a second linkage 74 laterally and pivotally connected to one another. The linkage mechanism 70 provides movement of the arms 18 and 20 with respect to one another, thereby allowing inwardly and outwardly adjustment of the gripping surfaces 114, 116. The linkage mechanism 70 allows for accurate, precise incremental adjustment of the gripping area 12, while providing an improved gripping strength compared to the prior art.

FIGS. 15-18 provides a second embodiment of a gripping device 110 according to the present invention. The device 110 is designed principally the same as the device 10, with the exception that the adjustment arm/ratcheting mechanism has been modified.

Figure 15:
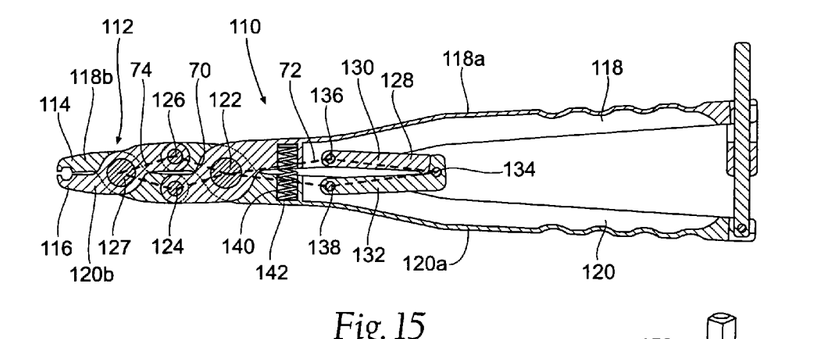
FIG. 15 is a cross-sectional view of an alternate embodiment of the present invention, also demonstrating the linkage mechanism used to control the gripping movement of the device.

FIG. 15 provides a cross-sectional view of the gripping device 110. As with the description of the previous embodiment 10 in FIG. 14, the gripping device 110 also has a double linkage mechanism 70 comprised a first linkage 72 and a second linkage 74 to control movement of the gripping device 110. The device 110 generally comprises a gripping section 112 that comprises a pair of opposed gripping surfaces, 114 and 116. The device further comprises a first arm 118 and a second arm 120 for physically manipulating the gripping device 110. The arms 118, 120 generally comprise a respective rear section 118a, 120a and a respective front section 118b, 120b. The rear sections 118a, 120b allow the user to manipulate, grasp, and move the arms 118, 120, while the front sections 118b, 120b provide the necessary gripping arrangement for the gripping section 112.

The rear sections 118a and 120a of the arms 118 and 120 are connected by a fulcrum 122, which is where the first linkage 72 is connected to the second linkage 74. A secondary pivot 124 connects the rear section 118a to the front section 118b, while a pivot 126 connects the rear section 120a to the front section 120b. The front sections 118b, 120b are pivotally connected to one another with a second fulcrum 127, which assists in translating up and down movement of the rear sections 118a and 120a into gripping movement for the gripping section 112. The dual scissors arrangement of the arms 118 and 120 further comprises the dual linkage mechanism 70, with the first linkage 72 comprising a scissors style member 128, which has a first leg 130 and a second leg 132 that are connected to one another by a pivot 134. The first leg 130 is pivotally connected to the arm 118 by way of a pivot 136, and the second leg 132 is connected to the arm 120 by way of a pivot 138. A spring 140 located within a housing 142 biases the arms 118 and 120 against one another and contributes to the overall precision for the gripping device 110.

Figure 16:
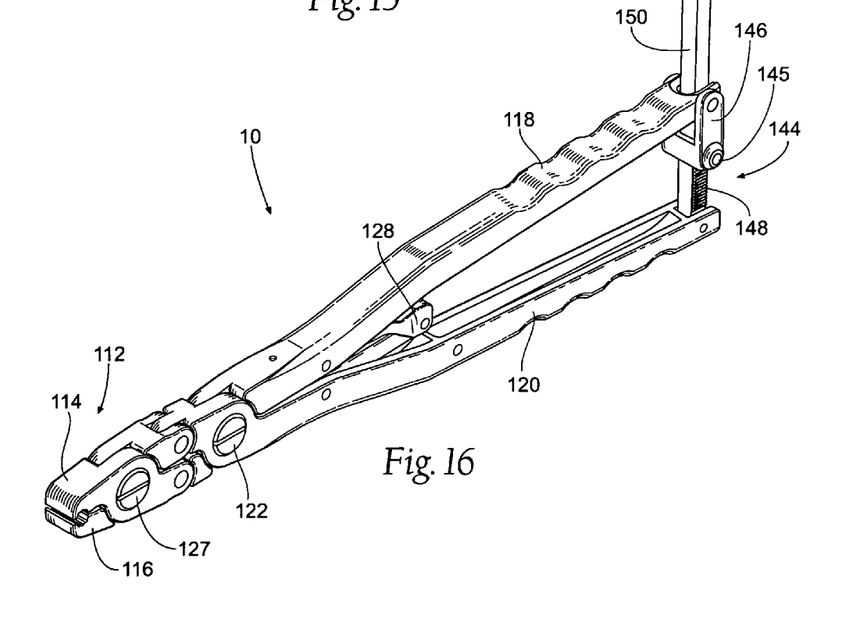
FIG. 16 is a front perspective view of the alternate embodiment shown in FIG. 15.

As discussed with respect to FIG. 15, the gripping devices 10 and 110 operate in the same fashion. The adjustment and positioning of the devices 10 and 110 is similar between the two devices, as well, with the major difference being the location of a ratcheting mechanism for the devices. FIG. 16 provides a perspective view of the gripping device 110, with a ratcheting mechanism 144 releasably connecting the arm 118 to the arm 120. The ratcheting mechanism 144 generally comprises a pawl 146 that will interact with a plurality of notched or teeth 148 to adjust the separation of the arms 118 and 120. A press button 145 can be employed to release the ratcheting mechanism 144, if necessary. The teeth 148 are supported by a post 150 that is pivotally secured to the arm 120. The post 150 intersects the arm 118 through a receptacle 152. The pawl 146 is connected to the arm 118, and is capable of holding the arms 118 and 120 a selected distance apart from one another, with the ratcheting mechanism 144 allowing the user to precisely bring the gripping surfaces 114 and 116 towards one another.

Figure 17:
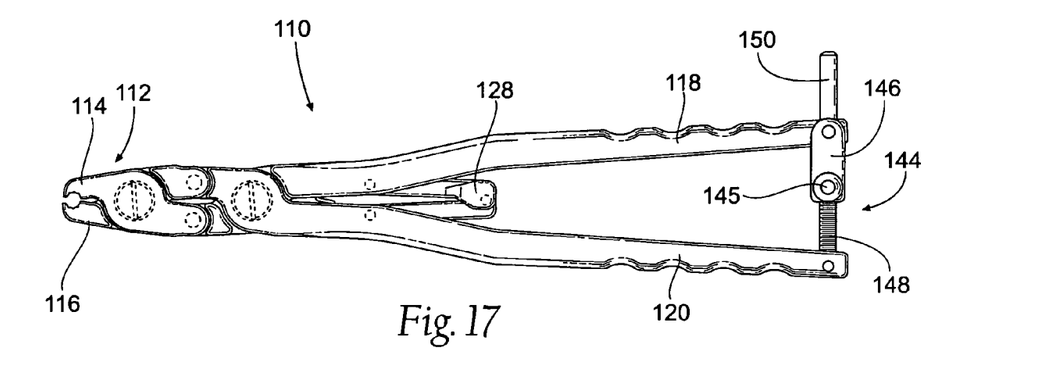
FIG. 17 is a side elevation view of the device shown in FIG. 16.

FIG. 17 provides a side view of the gripping device 110. The ratcheting mechanism 144 is located at the rear of the arms 118 and 120, as opposed to centrally located on the arms 118 and 120, as was the arrangement for the gripping device 10 (see FIGS. 5 and 6). However, the operation of the ratcheting mechanisms is similar. Further, the ratcheting mechanism 144 also allows for adjustment of the spacing of the arms 118 and 120, similar to the adjustment arm 36 of the gripping device 10 (see FIG. 9). While the ratcheting mechanism 114 could be located anywhere along the arms 118 and 120, the positioning of the ratcheting mechanism 144 at the rear of the arms 118 and 120 allows the ratcheting mechanism 144 to act as an adjustment device as well.

Figure 18:
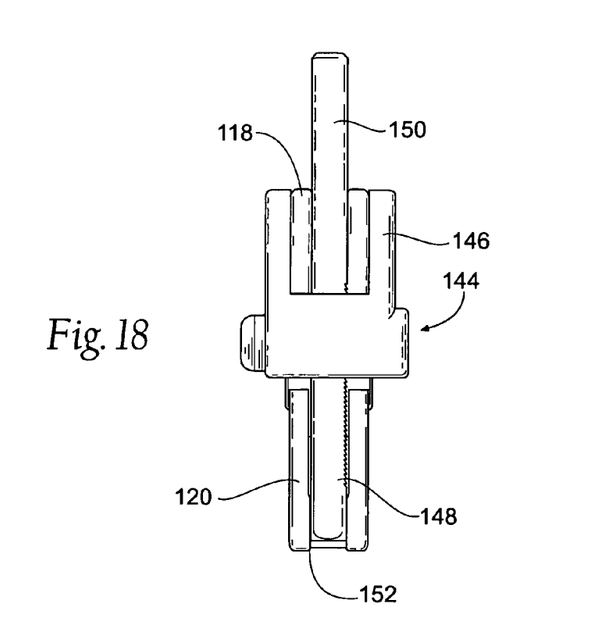
FIG. 18 is a rear elevation view of the device shown in FIG. 16.

FIG. 18 shows a rear elevation view of the ratcheting mechanism 144. The post 150 is connected to the arm 120 with a pin 152 that allows the post 150 to rotate inwardly and outwardly if necessary, similarly to the adjustment arm 36, shown in FIGS. 5-7. The pawl 146 is secured to the arm 118, and the post 150 slides through the pawl 146, thereby allowing the teeth 148 and the pawl 146 to interact and lock the device 110 at various positions.

The present invention provides a gripping device that provides precise gripping capabilities, while also having a gripping strength approximately twice of similar prior art designs. The integration of the positioning mechanism, i.e. the linkage mechanism, with the arms of the device (18, 20 or 118, 120) contributes to the improved precision and strength of the present invention. That is while it is possible that the linkage mechanism is a different structure than the arm of the device, preferably they are integrated structures, which work together to provide the movement for the device.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A gripping device comprising:
   a first arm having a front section and a rear section, said front and said rear section being pivotally connected to one another;
   a second arm having a front section and a rear section, said front and said rear section being pivotally connected to one another;
   a first fulcrum for pivoting said first arm front section with respect to said second arm front section;
   a second fulcrum for pivoting said first arm rear section with respect to said second arm rear section;
   wherein said first arm front section and said second arm front section providing opposing gripping surfaces for said device;
   a third fulcrum for pivoting a pair of positioning members with respect to one another, said pair of positioning members positioned between said first arm rear section and said second arm rear section, wherein a first positioning member of said pair of positioning members is pivotally attached to said first arm rear section at a first positioning pivot point and wherein a second positioning member of said pair of positioning members is pivotally attached to said second arm rear section at a second positioning pivot point, and wherein said first positioning member and said second positioning member are pivotally connected at said third fulcrum;
   wherein portions of said arms and said positioning members forming a linkage mechanism for moving said first arm with respect to said second arm, said positioning mechanism comprising a pair of laterally arranged linkages that are pivotally and laterally connected to one another at said second fulcrum,
   wherein a first linkage of said pair of laterally arranged linkages begins at said third fulcrum and terminates at said second fulcrum, and
   wherein a second linkages of said pair of laterally arranged linkages begins at said first fulcrum and terminates at said second fulcrum; and
   an adjusting means for adjusting the distance between said gripping surfaces.

2. The gripping device according to claim 1, further comprising means for biasing said first arm against said second arm.

3. The gripping device according to claim 1, wherein said adjusting means further comprises an adjustable arm connected to one of said first and said second arms, said adjustable arm capable of intersecting the other of said first and said second arms.

4. The gripping device according to claim 1 further comprising a positioning member, said positioning member comprising:
   a first leg pivotally connected to said first arm of said gripping device;
   a second leg pivotally connected to said second arm of said gripping device, said first leg and said second leg of said positioning member being pivotally connected to one another.

5. A gripping device comprising:
   a first arm having a front section and a rear section, said front and said rear section being pivotally connected to one another;
   a second arm having a front section and a rear section, said front and said rear section being pivotally connected to one another;
   a first fulcrum for pivoting said first arm front section with respect to said second arm front section;
   a second fulcrum for pivoting said first arm rear section with respect to said second arm rear section;
   wherein said first arm front section and said second arm front section providing opposing gripping surfaces for said device;
   means for biasing said first arm against said second arm; and
   a third fulcrum for pivoting a pair of positioning members with respect to one another, said pair of positioning members positioned between said first arm rear section and said second arm rear section, wherein a first positioning member of said pair of positioning members is pivotally attached to said first arm rear section at a first positioning pivot point and wherein a second positioning member of said pair of positioning members is pivotally attached to said second arm rear section at a second positioning pivot point, and wherein said first positioning member and said second positioning member are pivotally connected at said third fulcrum;
   wherein portions of said arms and said positioning members forming a linkage mechanism for moving said first arm with respect to said second arm, said positioning mechanism comprising a pair of laterally arranged linkages that are pivotally and laterally connected to one another at said second fulcrum,
   wherein a first linkage of said pair of laterally arranged linkages begins at said third fulcrum and terminates at said second fulcrum, and
   wherein a second linkage of said pair of laterally arranged linkages begins at said first fulcrum and terminates at said second fulcrum.

6. The gripping device according to claim 5 further comprising:
   an adjustable arm connected to one of said first and said second arms, said adjustable arm capable of intersecting the other of said first and said second arms, said adjustable arm capable of adjusting the distance between said gripping surfaces.

7. The gripping device according to claim 6, wherein said adjustable arm is pivotally connected to one of said first and said second arms.

8. The gripping device according to claim 5 wherein said first linkage of said double linkage system corresponds to where said rear sections are connected to one another, said second linkage corresponds to where said front sections are connected to one another.

9. The gripping device according to claim 5 further comprising releasable locking means for adjusting the distance between said gripping surfaces.

10. The gripping device according to claim 9 wherein said adjusting means further comprises a releasable ratcheting mechanism.

11. The gripping device of claim 1 wherein said adjusting means comprises a ratcheting mechanism, said ratcheting mechanism comprising:
   a notch member extending from said first arm towards said second arm, said notch member having a plurality of notches formed in said notch member; and
   a pawl member that extends from said second arm, wherein said pawl has an aperture for receiving said notch member therethrough and engaging one of said plurality of notches.

* * * * *

UNITED STATES PATENT AND TRADEMARK OFFICE
CERTIFICATE OF CORRECTION

PATENT NO. : 8,393,254 B2
APPLICATION NO. : 12/380823
DATED : March 12, 2013
INVENTOR(S) : Hua Gao It is certified that error appears in the above-identified patent and that said Letters Patent is hereby corrected as shown below:

In the Claims

Column 6, line 5 of claim 11, after "said notch member" delete "haying" and substitute -- having --.

Signed and Sealed this
Fourteenth Day of May, 2013

Teresa Stanek Rea
*Acting Director of the United States Patent and Trademark Office*